United States Patent
Kim et al.

(10) Patent No.: US 10,492,889 B2
(45) Date of Patent: Dec. 3, 2019

(54) RAPID PROTOTYPED TRANSFER TRAY FOR ORTHODONTIC APPLIANCES

(71) Applicant: 3M INNOVATIVE PROPERTIES COMPANY, St. Paul, MN (US)

(72) Inventors: Sung Kim, San Francisco, CA (US); Richard E. Raby, Lino Lakes, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/261,281

(22) Filed: Sep. 9, 2016

(65) Prior Publication Data

US 2016/0374779 A1 Dec. 29, 2016

Related U.S. Application Data

(63) Continuation of application No. 14/820,032, filed on Aug. 6, 2015, which is a continuation of application
(Continued)

(51) Int. Cl.
*A61C 3/00* (2006.01)
*A61C 7/14* (2006.01)
(Continued)

(52) U.S. Cl.
CPC .............. *A61C 7/146* (2013.01); *A61C 7/002* (2013.01); *B29C 64/188* (2017.08);
(Continued)

(58) Field of Classification Search
CPC ........... A61C 7/002; A61C 7/146; A61C 7/00; A61C 7/02
(Continued)

(56) References Cited

U.S. PATENT DOCUMENTS

| 3,949,477 A | 4/1976 | Cohen |
| 4,626,208 A * | 12/1986 | Hall ................ G01S 13/755 433/3 |

(Continued)

FOREIGN PATENT DOCUMENTS

| DE | 10-2007-036549 | 2/2008 |
| EP | 2266494 A1 | 12/2010 |

(Continued)

OTHER PUBLICATIONS

"Rapid prototyping: A new method of preparing trays for indirect bonding"; American Journal of Orthodontics and Dentofacial Orthopedics; vol. 129, No. 1, Jan. 2006; Ciuffolo et al., pp. 75-77.

(Continued)

*Primary Examiner* — Matthew M Nelson

(57) ABSTRACT

The present invention is directed to computer-implemented methods of making a transfer tray using rapid prototyping techniques, where the gingival edge of the tray is defined to intersect with at least one receptacle for receiving an orthodontic appliance. This tray configuration helps to minimize the travel distance of the tray when placing the tray over a patient's teeth, while also preserving a high degree of mechanical retention for retaining the appliance until such time that the appliance is bonded to the tooth. Other aspects of the tray and associated methods of bonding are directed to a frangible web that extends over the gingival portion of the receptacle and fractures to facilitate tray removal after bonding.

5 Claims, 9 Drawing Sheets

Related U.S. Application Data

No. 12/997,663, filed as application No. PCT/US2009/047430 on Jun. 16, 2009, now abandoned.

(60) Provisional application No. 61/075,831, filed on Jun. 26, 2008.

(51) Int. Cl.

| | |
|---|---|
| *B33Y 50/00* | (2015.01) |
| *B29C 64/393* | (2017.01) |
| *B29C 64/188* | (2017.01) |
| *A61C 7/00* | (2006.01) |
| *G05B 19/4099* | (2006.01) |
| *B33Y 10/00* | (2015.01) |
| *B33Y 80/00* | (2015.01) |
| *B33Y 50/02* | (2015.01) |

(52) U.S. Cl.
CPC ............ *B29C 64/393* (2017.08); *B33Y 10/00* (2014.12); *B33Y 50/00* (2014.12); *B33Y 80/00* (2014.12); *G05B 19/4099* (2013.01); *B33Y 50/02* (2014.12); *G05B 2219/35134* (2013.01); *G05B 2219/49007* (2013.01)

(58) Field of Classification Search
USPC .................................................... 433/8–24
See application file for complete search history.

(56) References Cited

U.S. PATENT DOCUMENTS

| | | | |
|---|---|---|---|
| 4,657,508 A * | 4/1987 | Dellinger ............... | A61C 7/146 433/24 |
| 4,672,032 A | 6/1987 | Slavkin | |
| 5,204,055 A | 4/1993 | Sachs | |
| 5,340,656 A | 8/1994 | Sachs | |
| 5,387,380 A | 2/1995 | Cima | |
| 5,431,562 A | 7/1995 | Andreiko | |
| 5,447,432 A | 9/1995 | Andreiko | |
| 5,454,717 A | 10/1995 | Andreiko | |
| 5,490,882 A | 2/1996 | Sachs | |
| 5,490,962 A | 2/1996 | Cima | |
| RE35,169 E | 3/1996 | Lemchen | |
| 5,518,680 A | 5/1996 | Cima | |
| 5,700,289 A | 12/1997 | Breitbart | |
| 5,711,665 A * | 1/1998 | Adam ...................... | A61C 7/16 433/24 |
| 5,971,754 A * | 10/1999 | Sondhi ................... | A61C 7/146 433/24 |
| 6,123,544 A * | 9/2000 | Cleary ................... | A61C 7/146 433/24 |
| 6,565,355 B2 * | 5/2003 | Kim ....................... | A61C 7/145 433/3 |
| 6,739,869 B1 | 5/2004 | Taub | |
| 6,776,614 B2 | 8/2004 | Wiechmann | |
| 7,020,963 B2 | 4/2006 | Cleary | |
| 7,137,812 B2 | 11/2006 | Cleary | |
| 7,168,950 B2 | 1/2007 | Cinader, Jr. | |
| 7,354,268 B2 | 4/2008 | Raby | |
| 7,449,499 B2 | 11/2008 | Craig | |
| 7,452,924 B2 | 11/2008 | Aasen | |
| 7,726,968 B2 | 6/2010 | Raby | |
| 7,845,938 B2 * | 12/2010 | Kim ....................... | A61C 7/146 433/3 |
| 7,910,632 B2 | 3/2011 | Cinader, Jr. | |
| 8,992,215 B2 | 3/2015 | Chapoulaud | |
| 2003/0003415 A1 * | 1/2003 | Kim ....................... | A61C 7/145 433/3 |
| 2004/0229185 A1 * | 11/2004 | Knopp .................... | A61C 7/146 433/3 |
| 2005/0074716 A1 * | 4/2005 | Cleary ................... | A61C 7/146 433/3 |
| 2005/0175966 A1 | 8/2005 | Falsafi | |
| 2005/0208450 A1 * | 9/2005 | Sachdeva ................ | A61C 7/00 433/24 |
| 2005/0233276 A1 * | 10/2005 | Kopelman ............... | A61C 7/08 433/3 |
| 2006/0024637 A1 | 2/2006 | Raby | |
| 2006/0084026 A1 * | 4/2006 | Cinader ................. | A61C 7/146 433/24 |
| 2006/0084030 A1 | 4/2006 | Phan et al. | |
| 2006/0177791 A1 * | 8/2006 | Cinader, Jr. .......... | A61C 7/146 433/24 |
| 2006/0223021 A1 * | 10/2006 | Cinader, Jr. .......... | A61C 7/146 433/3 |
| 2007/0031775 A1 | 2/2007 | Andreiko | |
| 2007/0087302 A1 * | 4/2007 | Reising ................. | A61C 7/145 433/24 |
| 2007/0238064 A1 | 10/2007 | Stark | |
| 2008/0096151 A1 | 4/2008 | Cinader, Jr. | |
| 2008/0227050 A1 * | 9/2008 | Marshall ................ | A61C 7/00 433/24 |
| 2009/0017410 A1 | 1/2009 | Raby | |
| 2010/0216083 A1 | 8/2010 | Grobbee et al. | |

FOREIGN PATENT DOCUMENTS

| | | | |
|---|---|---|---|
| JP | 2001061865 | | 3/2001 |
| JP | 2001061865 A | * | 3/2001 |
| KR | 2002-0004333 | | 1/2002 |
| WO | WO 01/85047 A2 | | 11/2001 |

OTHER PUBLICATIONS

International Search Report PCT/US2009/047430; Sep. 15, 2009, 5 pgs.

* cited by examiner

RAPID PROTOTYPED TRANSFER TRAY FOR ORTHODONTIC APPLIANCES

CROSS REFERENCE TO RELATED APPLICATIONS

This application is a continuation of U.S. application Ser. No. 14/820,032, filed Aug. 6, 2015, now pending, which is a continuation of U.S. application Ser. No. 12/997,663, filed Dec. 13, 2010, now abandoned, which is a national stage filing under 35 U.S.C. 371 of PCT/US2009/047430, filed Jun. 16, 2009, which claims priority to U.S. Provisional Application No. 61/075,831, filed Jun. 26, 2008, the disclosure of which are incorporated by reference in their entirety herein.

BACKGROUND OF THE INVENTION

1. Field of the Invention

This invention relates to transfer trays that are used by orthodontic treating professionals to bond appliances to the teeth of an orthodontic patient. The invention is also related to methods for making such transfer trays.

2. Description of the Related Art

Orthodontics is the area and specialty of dentistry associated with the supervision, guidance and correction of malpositioned teeth to desired locations in the oral cavity. Orthodontic treatment can improve the patient's facial appearance, especially in instances where the teeth are noticeably crooked or where the upper and lower teeth are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and a resilient, generally U-shaped archwire is placed in the slot of each bracket. As the teeth are crooked, the archwire is deflected from its original shape as it is placed in the slot of each bracket. During treatment, the archwire gradually springs back to its original shape and, in so doing, urges the teeth to the desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The combination of brackets, buccal tubes and archwires is commonly referred to as "braces".

In many types of orthodontic techniques, the precise position of the appliances on the teeth is an important factor in predicting the final teeth positions. One common type of orthodontic technique is known as the "straight-wire" method, introduced by Dr. L. F. Andrews in 1972. In the "straight-wire" method, the set of appliances is configured such that the archwire lies in a horizontal plane at the conclusion of treatment. Consequently, the appliances must be correctly positioned at the beginning of treatment so that the teeth are properly aligned once the archwire straightens and lies in the horizontal plane. If, for example, a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

One technique for bonding orthodontic appliances to teeth is known as an indirect bonding technique. In the past, known indirect bonding techniques have often used a placement device or transfer apparatus having a shape that matches a configuration of at least a portion of the patient's dental arch. One type of transfer apparatus is called a "transfer tray" or "indirect bonding tray", and typically has an elongated cavity for simultaneously receiving a number of teeth. A set of appliances such as brackets is releasably connected to the inner surface of the tray at certain, predetermined locations.

During the use of a bonding tray for indirect bonding, an adhesive is typically applied to the base of each appliance by the orthodontist or a staff member. The tray is then placed over the patient's teeth and remains in place until such time as the adhesive hardens. Next, the tray is detached from the teeth as well as from the appliances, with the result that all of the appliances previously connected to the tray are now bonded to respective teeth at their intended, predetermined locations.

Indirect bonding trays are normally custom-made for each patient because the size and orientation of teeth can vary widely from one patient to the next. One method of making indirect bonding trays includes the steps of taking an impression of each of the patient's dental arches and then making a replica plaster or "stone" model from each impression. If desired, the teeth of the model can be marked with a pencil to assist in placing the brackets in ideal positions. Next, the brackets are temporarily bonded to the stone models using a suitable adhesive. An indirect bonding tray is then made by placing matrix material over the model as well as over the brackets on the model. For example, in a thermoforming method, a plastic sheet matrix material may be placed over the model and brackets and then heated in an oven under vacuum. As the plastic sheet material softens and as air in the oven is evacuated, the plastic sheet material assumes a configuration that precisely matches the shape of the replica teeth of the stone model and adjacent brackets. The plastic material is then allowed to cool and harden to form a tray. As an alternative to thermoforming, it is possible to cast a suitable resin, such as silicone, around the teeth of the model and then harden the resin to produce the tray. In this case, a casting vessel is sometimes used to contain the resin prior to hardening.

Once the tray has been formed, it is carefully detached from the stone replica, along with the associated appliances. When the tray is detached, the adhesive used to bond each appliance to the model is typically retained on the base of each appliance. This adhesive pad, also called the custom resin base, conforms closely with the bonding surface on the replica tooth. Finally, the transfer tray is cleaned and trimmed as may be desired to provide a proper fit in the mouth.

While the state of the art with respect to indirect bonding trays has advanced in recent years, there is a continuing need to improve the ease of making and using such bonding trays.

SUMMARY OF THE INVENTION

The preparation of transfer trays can be, unfortunately, both laborious and time-consuming for the treating professional or lab technician. The conventional process of either thermoforming or casting the tray requires the intervention of an operator and is subject to human error, particularly in the manual positioning of brackets on the model. Moreover, the steps of preparing a replica dental model, bonding appliances to the replica model, detaching the tray from the model, and eventually cleaning and trimming of the finished tray, each incur additional time or materials costs.

The present invention is directed in one aspect to a method of making a customized transfer tray for bonding orthodontic appliances to the teeth of an orthodontic patient. The tray is configured in the virtual world by defining the desired location of each orthodontic appliance and configuring a virtual transfer tray that fits over the teeth and includes a plurality of appliance receptacles that precisely locate each appliance in its respective desired location. The method further includes defining a gingival edge of the transfer tray such that the edge intersects each receptacle. A physical transfer tray is then formed using rapid prototyping techniques based on the exact configuration of the virtual transfer tray configured therefrom.

By configuring the gingival edge of the transfer tray to intersect each receptacle, the treating professional gains particular advantages during the bonding procedure. First, the transfer tray only partially encapsulates each appliance, thereby facilitating both engagement and disengagement of the transfer tray from appliances. Second, positioning the receptacles at the gingival edge of the transfer tray also reduces the travel distance of the tray during seating, thereby minimizing adhesive smearing during the bonding (particularly when using two-part chemical cure adhesives). This transfer tray may be pre-loaded with orthodontic appliances by the manufacturer or alternatively may be loaded by the treating professional prior to bonding. By automating the tray manufacturing based directly on digital data, this method also offers improved product consistency, compared with manually prepared transfer trays.

The transfer tray may also include a thin frangible web of material that partially extends across gingival portions of the appliance, such that the appliance is securely retained in the tray prior to bonding. Once the appliance has been bonded to the patient's dental structure, the frangible web can then be fractured and the tray removed from the patient's mouth by urging the transfer tray in the occlusal direction. The presence of a frangible web is particularly advantageous since it provides both convenient loading and retention of the appliance into the tray, as well as easy detachment of the tray from the patient's dental structure. Detachment of the tray in the occlusal direction is convenient and comfortable for the patient since it does not involve pulling the tray outward against the cheeks or lips. Occlusal tray removal is also helps minimize the risk of accidentally debonding the newly bonded appliances, since it avoids the need to pull the appliances away from the tooth surface in the labial direction (or lingual direction in the case of lingual appliances).

The use of rapid prototyping techniques to fabricate the transfer tray is advantageous because it provides the freedom for the receptacle geometry to be adapted for easy engagement and disengagement of the orthodontic appliance from the tray. Other known fabrication methods, such as casting and thermoforming, fully surround the appliance with a matrix material to form the shape of the receptacle. While this is effective in retaining the appliance, this configuration is also inherently disadvantageous since the strong mechanical retention of the appliance can result in detaching the appliances from the teeth as the tray is removed from the mouth. The risk of bond failures is oftentimes so significant that the treating professional or assistant is compelled to manually section the tray into several pieces to facilitate removing the tray from the mouth, which is a nuisance. The present invention provides both a high level of mechanical retention for precise positioning of the appliance prior to bonding, as well as rapid and easy disengagement of the tray from the mouth in one piece after bonding.

Other aspects of the tray derive from incorporating multiple materials, or components, into the transfer tray. Using two or more components is beneficial because each part of the tray has its own set of material requirements based on its particular function. For example, the transfer tray may include one or more stop members that specifically engage pre-determined portions of occlusal teeth surfaces during a bonding procedure. By forming stop member(s) from a material that is harder than the rest of the tray, it is possible to form a "positive hard stop" between the tray and the teeth, thereby providing increased accuracy in positioning each appliance on its respective tooth surface. As another example, the transfer tray may further include one or more receptacles that are formulated from relatively softer materials to facilitate release of appliances from the tray when detaching the transfer tray from the patient's teeth after bonding.

As a further advantage, rapid prototyping techniques provide greater freedom to construct components of the transfer tray independently of each other. These configurations may include spatial arrangements of stop members and/or receptacles that are difficult or impossible to fabricate using traditional thermoforming or casting methods. For example, transfer trays that are thermoformed or cast generally display at least one single continuous layer that extends across the entire tray. This need not be the case with trays formed by rapid prototyping, which may include, for example, patterned layers.

In another aspect, the present invention is directed to a method of making a transfer tray for indirect bonding an orthodontic appliance including obtaining a virtual model of a patient's dental structure, determining a desired location for a virtual orthodontic appliance on the model, placing a virtual appliance receptacle at the desired location, where the virtual receptacle has a configuration that matches at least a portion of the appliance, deriving a virtual tray body extending across at least a portion of the model and at least a portion of the receptacle remote from the model, where the act of deriving a virtual tray body includes the act of defining a gingival edge of the tray body that intersects the virtual receptacle, forming the transfer tray by rapid prototyping, where the transfer tray includes a physical tray body and a physical receptacle that correspond to the virtual tray body and virtual receptacle respectively.

In still another aspect, the invention is directed to a method of bonding an orthodontic appliance to a patient's dental structure, including obtaining a virtual model of a patient's dental structure, determining a desired location for a virtual orthodontic appliance on the model, placing a virtual appliance receptacle at the desired location, where the virtual receptacle has a configuration that matches at least a portion of the appliance, deriving a virtual tray body extending across at least a portion of the model and at least a portion of the receptacle remote from the model, where the act of deriving a virtual tray body includes the act of defining an gingival edge of the tray body that intersects the virtual receptacle. The method further includes forming the transfer tray by rapid prototyping, where the transfer tray includes a physical tray body and a physical receptacle that correspond to the virtual tray body and virtual receptacle respectively, placing the appliance in the physical receptacle, applying an adhesive to the surface of the orthodontic appliance, placing the transfer tray over the patient's dental structure, and hardening the adhesive.

In yet another aspect, the invention is directed to a method of bonding an orthodontic appliance to a patient's dental structure including providing an orthodontic transfer tray having a receptacle and an orthodontic appliance received in the receptacle, placing the transfer tray over the patient's dental structure, bonding the appliance to the patient's dental structure with an adhesive, and subsequently detaching the transfer tray from the appliance by urging the transfer tray in a generally occlusal direction, wherein the act of detaching the transfer tray includes fracturing a portion of the tray that extends across at least a portion of a gingival side of the receptacle.

DEFINITIONS

As used herein:
"Mesial" means in a direction toward the center of the patient's curved dental arch.
"Distal" means in a direction away from the center of the patient's curved dental arch.
"Occlusal" means in a direction toward the outer tips of the patient's teeth.
"Gingival" means in a direction toward the patient's gums or gingiva.
"Facial" means in a direction toward the patient's lips or cheeks.
"Lingual" means in a direction toward the patient's tongue.

DETAILED DESCRIPTION OF THE PREFERRED EMBODIMENTS

As used herein, a "virtual" object includes digital data that represents, defines or renders a viewable 3D model of the object, or the model itself. In the examples below, the concepts of a "virtual object", "virtual model" and "digital image" are used interchangeably. Virtual objects can be stored, processed, and/or communicated using a back office server or workstation, such as a general purpose computer having a processor capable of manipulating digital images, a user interface, and a display to allow a user to view digital images. The computer further includes memory that is capable of storing multiple sets of virtual models and fully accessible to software running on the computer. The rapid prototyping machine and computer are typically located in the same place, but this need not be the case. Since digital information can be transferred over a wired data connection or the Internet, data representing a patient's dental structure may be acquired and manipulated in the office of the treating professional, and the transfer tray itself manufactured using an off-site rapid prototyping machine.

Figure 1:
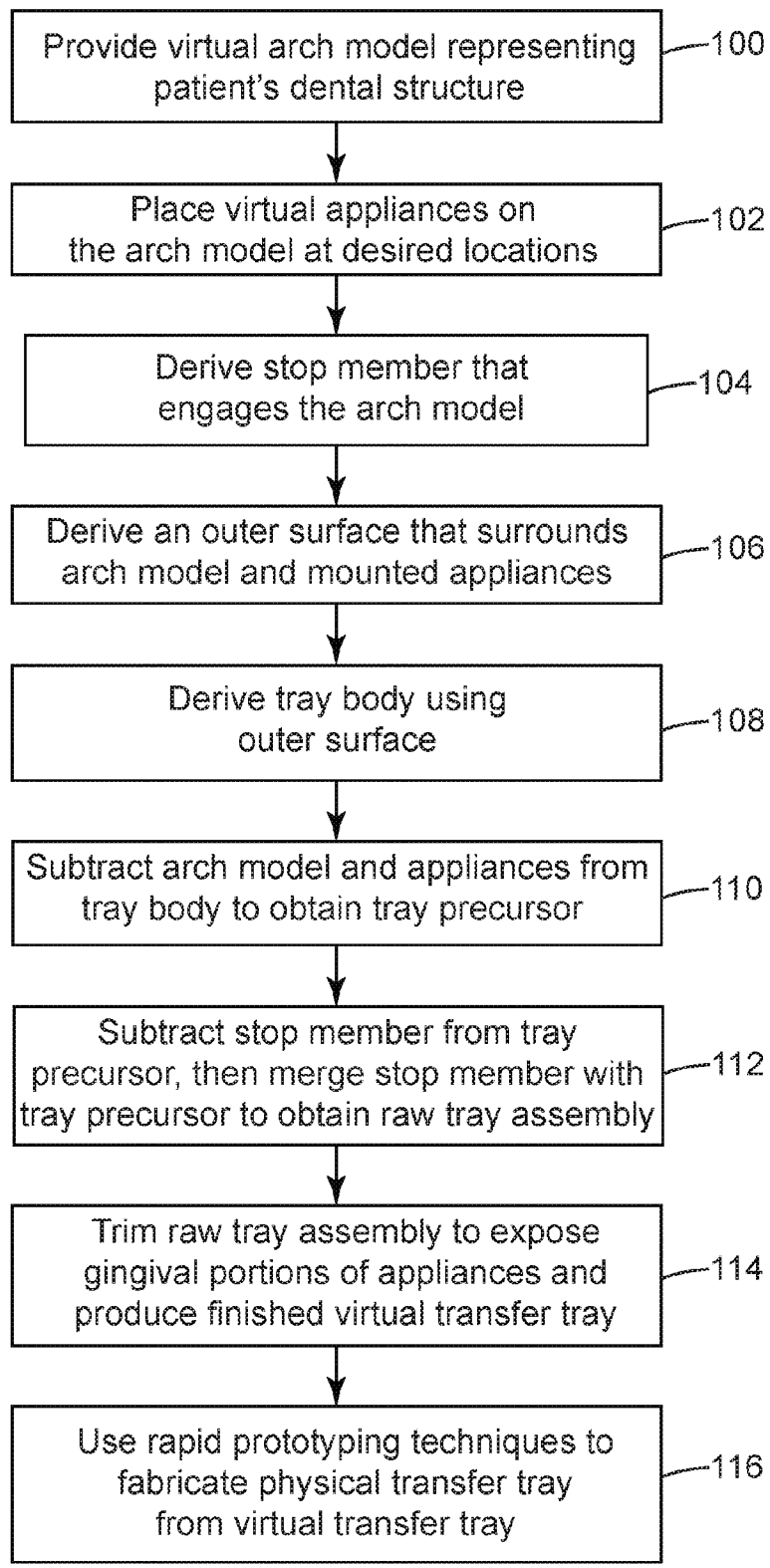
FIG. 1 is a block diagram illustrating a method of making a physical transfer tray according to one embodiment of the invention.
Figure 2:
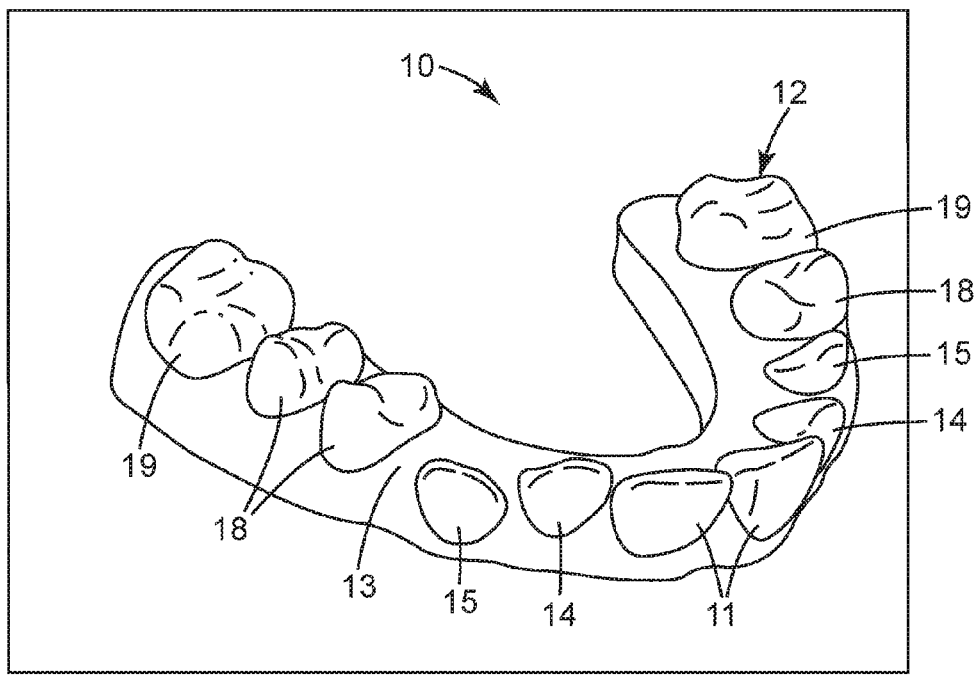
FIG. 2 is a perspective view of an exemplary virtual dental model.

FIG. 1 is a schematic block diagram describing a workflow used to make a transfer tray for placing orthodontic appliances on a patient's teeth according to exemplary embodiments of the present invention. The first block, designated by the numeral 100, represents the step of providing a virtual model of a patient's dental structure. FIG. 2 shows a virtual model 10 derived in block 100 as might be seen on a computer display. As shown, the model 10 represents the inverted upper arch of a patient and includes a plurality of teeth 12. In more detail, the teeth 12 include left and right central teeth 11, lateral teeth 14, cuspid teeth 15, bicuspid teeth 18, and first molar teeth 19, as well as surrounding gingival tissues 13. In this particular dental arch, there are two bicuspid teeth 18 on the left side but only a single biscuspid tooth 18 on the right side.

Model 10 can be obtained using digital data provided using a hand-held intra-oral scanner such as the intra-oral scanner using active wavefront sampling developed by Brontes Technologies, Inc. (Lexington, Mass.). Alternatively, other intra-oral scanners or intra-oral contact probes may be used. As another option, the digital data may be obtained by scanning an impression or other negative replica of the patient's dental structure. As still another option, the model 10 may be obtained by scanning a positive replica of the dental structure or by using a contact probe on the positive replica. The positive replica used for scanning may be made by pouring a casting material (such as plaster of Paris or epoxy resin) into an impression of the patient's teeth and allowing the casting material to cure. If scanning is used, any suitable scanning technique may then be used to obtain the model 10, including X-ray scanning, laser scanning, computed tomography (CT), and magnetic resonance imaging.

Additional steps may be used to further refine the digital data before rendering the model. For example, the digital data representing model 10 may be additionally filtered or processed by removing erroneous data points. For example, STL (stereolithography) data files representing a tooth surface that include a data point significantly outside the normal expected geometrical relationship of adjacent data points could be fixed by STL-handling software to remove the erroneous data point. In addition, tooth data points that are missing could be added by software that manipulates STL files to create realistic, smoothly curved tooth shapes. In some embodiments, data processing is carried out before conversion of the data to an STL file.

Figure 3:
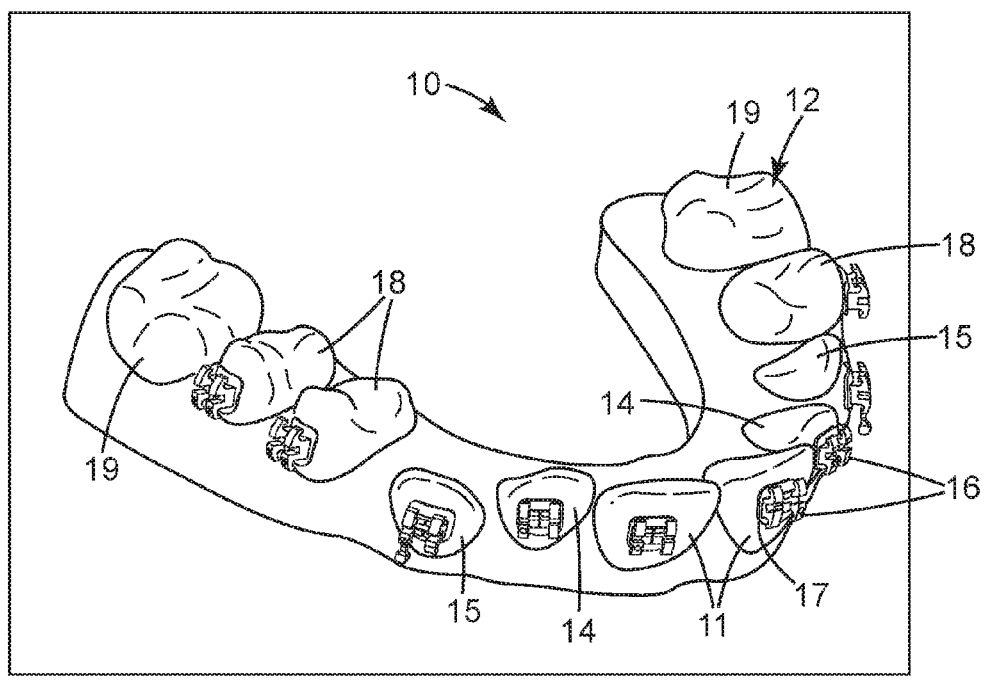
FIG. 3 is a perspective view of a composite model including virtual orthodontic appliances mounted on the model of FIG. 2.

The workflow then proceeds to block 102, where one or more virtual appliances are placed at desired locations on the teeth 12 of model 10 to form a composite model. This composite model is illustrated in FIG. 3 and shows virtual orthodontic appliances 16 connected to the virtual central teeth 11, lateral teeth 14, cuspid teeth 15, and bicuspid teeth 18 of the model 10. Although not shown here, one or more bondable molar appliances can optionally be connected to the virtual molar teeth 19 of the model 10. In the present embodiment, the appliances 16 are represented by labial brackets. However, appliances 16 may also include lingual brackets, molar tubes, buttons, cleats, sheaths, or any other orthodontic appliances suitable for bonding to the surfaces of teeth. In some embodiments, the appliances 16 are directly provided in the form of an STL file, or other digital image, by the appliance manufacturer. Alternatively, the digital images representing the appliances 16 may provided by scanning the physical appliance, or appliances, themselves. Preferably, the appliances 16 are exact virtual replicas of the physical appliances to be bonded to the teeth of the patient.

As shown, each appliance 16 includes a virtual base 17 which in turn has a tooth-facing surface that contacts a respective tooth 12 when the appliance 16 is positioned in its desired location. Each appliance 16 may be a based on a standardized "off-the-shelf" bracket or, alternatively, may be custom made according to the unique dental structure of the patient. In the latter case, the base 17 of each appliance 16 preferably includes a tooth-facing surface contour that exactly matches that of its respective tooth 12 when the appliance is in its desired location. Examples of customized orthodontic appliances in the art include U.S. Pat. No. 6,776,614 (Weichmann et al.), RE35,169 (Lemchen et al.), U.S. Pat. No. 5,447,432 (Andreiko et al.), U.S. Pat. No. 5,431,562 (Andreiko et al.), and U.S. Pat. No. 5,454,717 (Andreiko et al.).

The desired locations for the appliances 16 on the model 10 can be determined in any of a number of ways. In one example, the treating professional manually selects and places the virtual appliances 16 directly on the model 10 using the local computer. In some embodiments, the modeling software treats each appliance 16 and each tooth 12 as a separate object within the 3D environment and fixes the position of each appliance 16 within the 3D space relative to a coordinate system associated with the tooth 12 of the corresponding appliance 16. The modeling software can then, for example, virtually connect the appliances 16 to a virtual archwire selected by the practitioner and compute the final positions of the teeth 12 based on the positions of the appliances 16 and the selected archwire. The modeling software can then display the virtual teeth 12 in their final occlusion for review by the treating professional.

If the treating professional is not entirely satisfied with the final predicted positions of the teeth, the treating professional may use the modeling software to manipulate one or more of the virtual appliances 16 relative to the teeth 12. Based on these adjustments, the modeling software can again virtually connect the appliances 16 to the virtual archwire, for example, to simulate the movement of teeth to new final positions. The new final positions of the teeth 12, determined by the positions of corresponding appliances 16, are then computed and displayed for review. These steps can be repeated as many times as desired until the treating professional is satisfied with the final positions of the teeth 12 as represented by the modeling software. As an alternative to moving appliances, the treating professional may instead use the modeling software to define the desired positions of teeth 12, and have the modeling software determine the suitable locations to place the appliances 16 in order to move the teeth 12 to those desired positions. Examples of virtual orthodontic treatment are disclosed in issued U.S. Pat. No. 6,739,869 (Kopelman et al.), U.S. Pat. No. 7,354,268 (Raby et al.) and published U.S. Patent Application No. 2008/0096151 (Cinader, Jr. et al.).

As another option, the steps in block 102 may be carried out by a technician at a location remote from the treating professional's office. For example, a technician at the appliance manufacturer's facility may use the modeling software to place appliances 16 on the model 10 based on standards or guidelines from an orthodontic treatment philosophy, such as for example that of Drs. MacLaughlin, Bennett, and Trevisi. These standards or guidelines for appliance placement may be specific to each tooth 12 in model 10, and call out the position of the archwire slot (an occlusal-gingival height, for example) with respect to the clinical crown of each tooth 12. The technician may also place appliances 16 in accordance with particular instructions provided by the treating professional. Once the technician is satisfied with the appliance positions and the resulting finished positions of the teeth, the model 10, together with the data representing the positions of appliances 16, are transmitted to the treating professional for review. The treating professional can then either approve the technician's appliance placement positions or reposition the appliances 16 as desired.

As yet another option, the local computer can automatically suggest locations of appliances 16 on the teeth 12 to the treating professional. Again, these proposed appliance locations are optionally based upon an orthodontic treatment philosophy or other known standards or guidelines in the art. Examples of automatically placing virtual brackets on teeth are described in issued U.S. Pat. No. 7,210,929 (Raby, et al.) and published U.S. Patent Application Nos. 2006/0024637 (Raby, et al.) and 2007/0238064 (Raby, et al.). As before, the treating professional has the opportunity to review the computer-proposed locations of appliances 16 and can either approve the placement positions or reposition the appliances 16 as desired.

Figure 4:
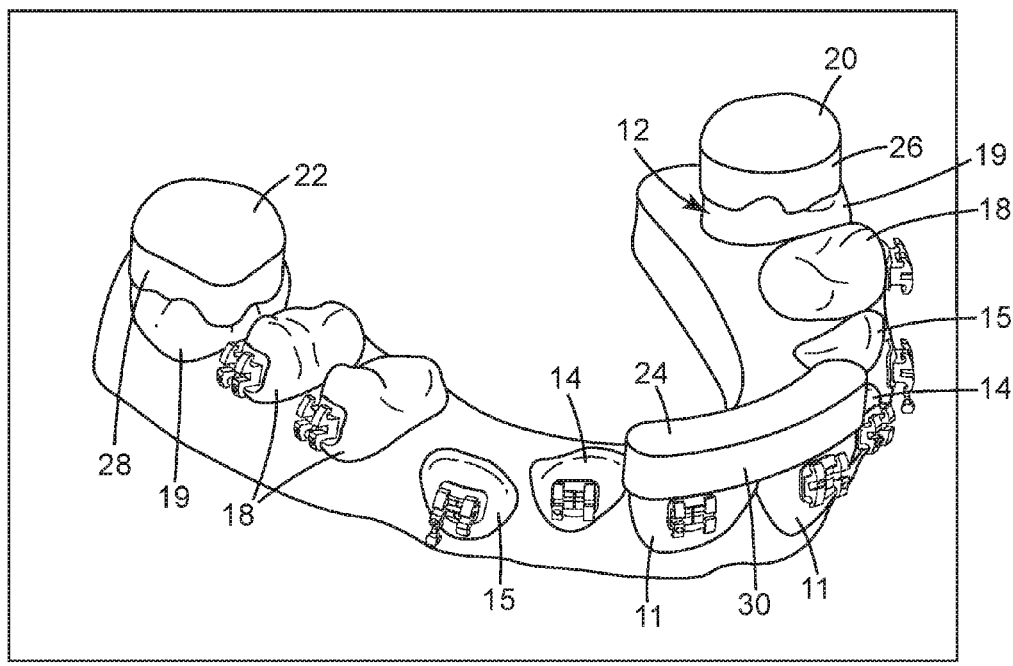
FIG. 4 is a perspective view showing the process of defining a virtual stop member that engages the composite model of FIG. 3.
Figure 5:
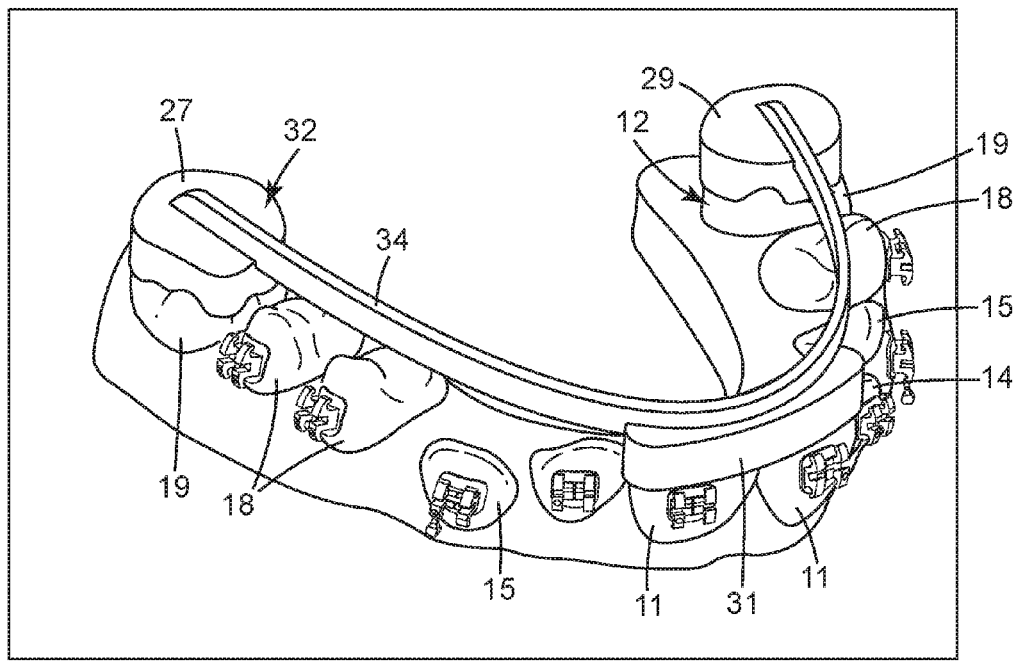
FIG. 5 is a perspective view showing the stop member of FIG. 4 in its finished configuration.

As indicated in block 104 and further illustrated in FIGS. 4 and 5, the local computer then derives a stop member 32 (FIG. 5) that virtually engages the teeth 12. This process proceeds as shown in FIG. 4 by defining a first generally oval-shaped surface 20 extending over the upper left first molar tooth 19, a second generally oval-shaped surface 22 extending over the upper right first molar tooth 19, and a third elongated surface 24 extending over the two upper central incisor teeth 11. The first, second, and third surfaces 20,22,24 may alternatively assume generally square, circular, or irregular shapes, if desired. Moreover, the surfaces 20,22,24 can be defined using a manual process, automatic process, or combination thereof. In a manual process, each surface 20,22,24 may be drawn by a technician, for example, using a mouse or other pointing device. In an automatic process, surfaces 20,22,24 may be defined by a software subroutine that isolates a given tooth object, projects the tooth object onto an occlusal plane of the model 10 to define a 2D surface, and then optionally scales the surface to extend across some or all of the occlusal surfaces of the tooth object.

The surfaces 20,22,24 are then aligned with the occlusal surfaces of their corresponding teeth 12, and virtually extruded towards the gingival direction until each surface 20,22,24 at least partially overlaps the crown(s) of the respective teeth 12. As shown, the surfaces 20,22,24 overlap to some degree with the underlying teeth 12 but stop short of overlapping any of the appliances 16. The extrusion of the surface 20, surface 22, and surface 24 sweeps out, in 3D space, first volume 26, second volume 28, and third volume 30, respectively. Once the first, second, and third volumes 26,28,30 have been defined, the model 10 is then virtually subtracted from each to produce respective posterior sections 27,29 and anterior section 31 as shown in FIG. 5. The posterior sections 27,29 and the anterior section 31 therefore have surface contours complemental to the occlusal surface contours of the respective underlying teeth 12. Optionally and as shown, a generally U-shaped flexible section 34 is additionally defined, which connects the posterior sections 27,29 and anterior section 31 to each other to form the integral stop member 32. The inclusion of the flexible section 34 advantageously registers the sections 27,29,31 with respect to each other in 3D space. The particular geometry of flexible section 34 furthermore provides particular advantages in the finished transfer tray, which shall be discussed later.

Figure 6:
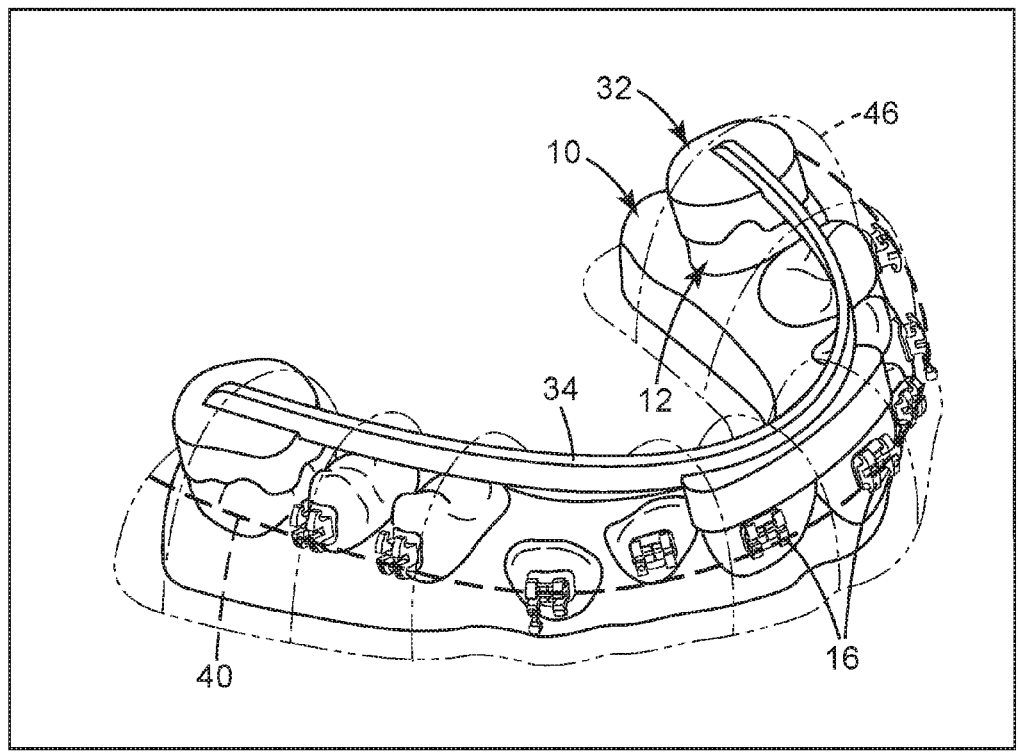
FIG. 6 shows the process of deriving a virtual outer surface over the composite model and stop member of FIG. 5.
Figure 7:
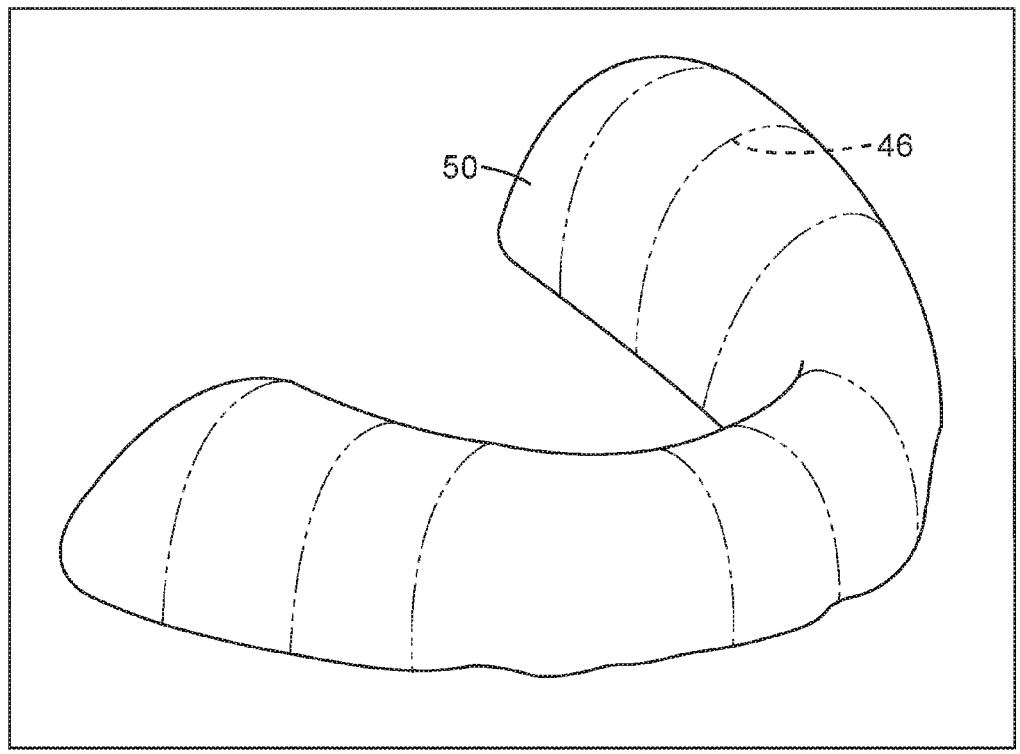
FIG. 7 is a perspective view showing the finished outer surface extending over the model and appliances of FIG. 5.

Next, block 106, along with FIGS. 6 and 7, illustrate the derivation of an outer surface that extends over both the model 10 and the stop member 32. In this embodiment, the derivation proceeds by defining a guidance line 40 that extends across at least a portion of the arch and is spaced away from the model 10 and mounted appliances 16. In the example shown, the guidance line 40 follows a curved path that is generally parallel to the facial surfaces of the appliances 16 and generally lies in an occlusal plane. However, one or more guidance lines 40 may also be defined which traverse the occlusal or lingual surfaces of the arch. In one computer-assisted embodiment, the guidance lines 40 are defined by tracing a line segment that connects the facial-most edges of appliances 16 as viewed from the occlusal direction, offsetting the line segment outwardly towards the facial direction by a certain distance and then applying a smoothing operation to the line segment. If desired, the certain distance can be used to define a desired tray thickness. The process in block 106 continues by defining a series of fitted arcs 46, each of which extends over the lingual, occlusal, and facial surfaces of the model 10 and intersects each guidance line 40 in a generally perpendicular relationship such that each fitted arc 46 passes over, without contacting, the model 10, mounted appliances 16, and stop member 32. In this example, each fitted arc 46 is generally semi-circular in shape and begins at a location lingual relative to the teeth 12 and terminates at a location facial to the teeth 12.

Figure 8:
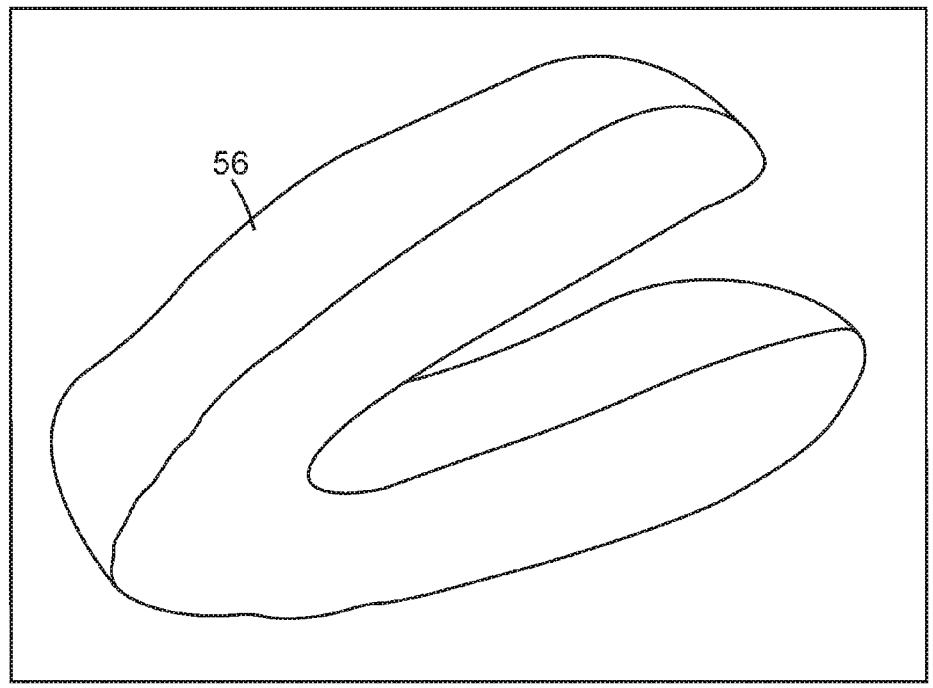
FIG. 8 is an inverted perspective view showing the outer shape of a virtual object that is derived from the finished outer surface of FIG. 7, illustrating gingival and facial sides.

FIG. 7 shows the derivation of the outer surface 50 from the fitted arcs 46. The outer surface 50 represents the exterior surface of the transfer tray and may be formed by fitting a surface to the set of fitted arcs 46. In some embodiments, the outer surface 50 is an open-ended shell that completely covers the occlusal, lingual, and facial sides of the assembly that includes the model 10, appliances 16, and stop member 32. Optionally, a surface smoothing operation is subsequently executed on the outer surface 50. Then, in block 108, a virtual tray body is derived using the outer surface 50. FIG. 8 shows the solid virtual tray body 56 formed by defining a composite surface that includes the outer surface 50 and a planar surface that extends across the cavity formed by the outer surface 50. When virtually aligned with the model 10, the tray body 56 surrounds both the teeth 12 and mounted appliances 16.

Figure 9:
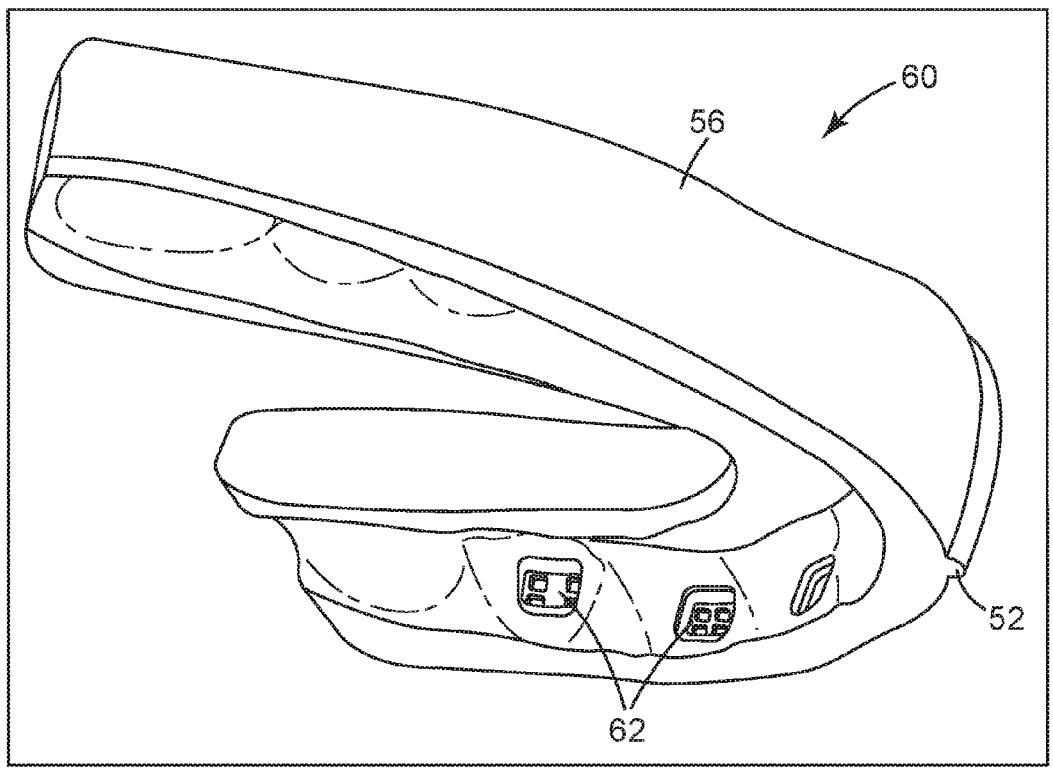
FIG. 9 is a perspective view of a virtual transfer tray precursor formed by subtracting the model and appliances of FIG. 3 from the outer shape of FIG. 8.

Next, block 110 shows the virtual subtraction of the model 10, along with mounted appliances 16, from the tray body 56 to produce a virtual tray precursor 60, which is shown in FIG. 9. Tray precursor 60 includes the tray body 56, which now has a shell-like configuration and further includes receptacles 62, formed by the negative virtual imprints of the appliances 16. As used herein, the term "receptacle" refers to a surface having a configuration that is sufficient to releasably retain an appliance. In some embodiments, the receptacle is at least partially complemental to the exterior surface of the appliance. Preferably, each receptacle 62 in the tray precursor 60 has a configuration that matches at least a portion of its respective appliance 16, allowing for precise and controlled securement between the resultant physical transfer tray and the physical appliances. If a tighter securement is desired between the physical transfer tray and the physical appliances, the receptacles 62 may optionally be scaled slightly smaller in one or more dimensions to provide an interference fit with the respective appliances 16. It is noted that this is possible because the physical tray can be fabricated using pliable materials that can slightly compress and/or expand to accommodate the physical appliances in the physical receptacles.

Optionally and as shown, a midline marker 52 is added to the tray precursor 60 to identify the location of the midline dividing the left and right quadrants of the teeth 12 in model 10. The midline marker 52 may be a raised ridge (as shown), bump, notch, groove, or any other visually prominent feature that corresponds to the midline position of the teeth 12. The corresponding physical marker can later assist the treating professional by providing visual indicator for aligning the finished physical transfer tray while placing the tray over the patient's dental structure.

Figure 10:
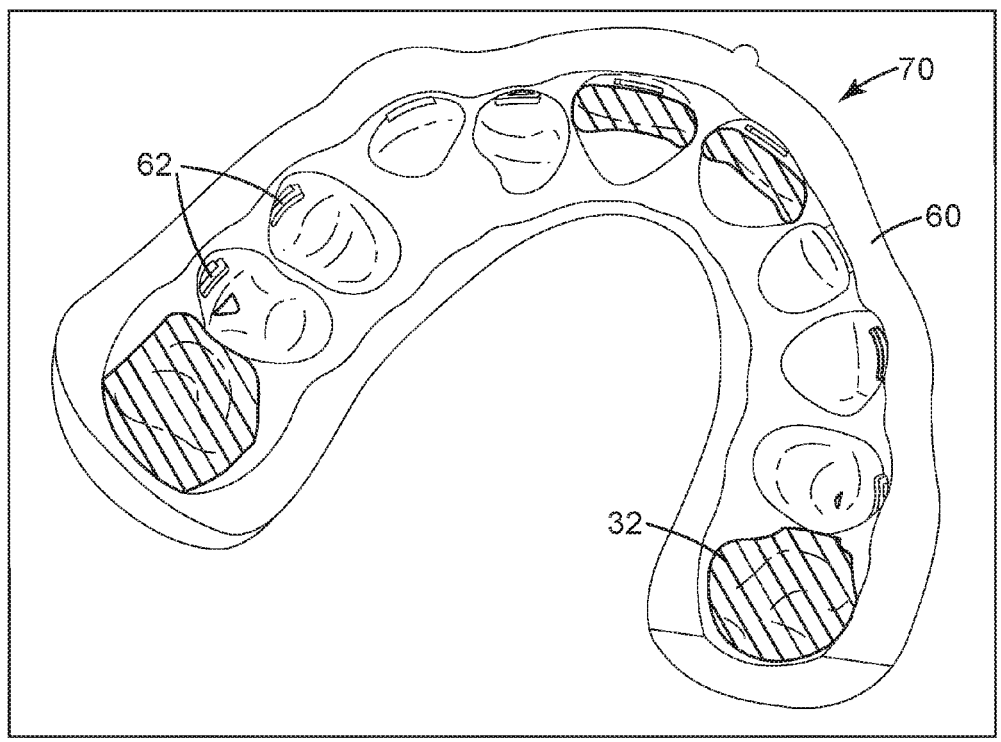
FIG. 10 is a gingival view of a virtual raw tray assembly formed by merging the tray precursor of FIG. 9 and stop member of FIG. 5.

Continuing with block 112, and as further illustrated in FIG. 10, the subset of data representing the stop member 32 is then subtracted from the data set representing the tray precursor 60, and the two resulting subsets finally merged back together to form the virtual tray assembly 70. The completion of this step results in a tray assembly 70 having a partially embedded stop member 32. It is noted from the figure that some occlusal surface regions of the stop member 32 are exposed when viewing the tray assembly 70 from the occlusal direction, and these are denoted as striped regions in this figure and in subsequent FIGS. 11, 11*a*, 12, and 15. When the tray assembly 70 is virtually engaged to model 10, the exposed portions of the stop member 32 precisely register with the occlusal surfaces of the molar teeth 19 and central teeth 11 in the manner shown in FIGS. 5-6.

Figure 11:
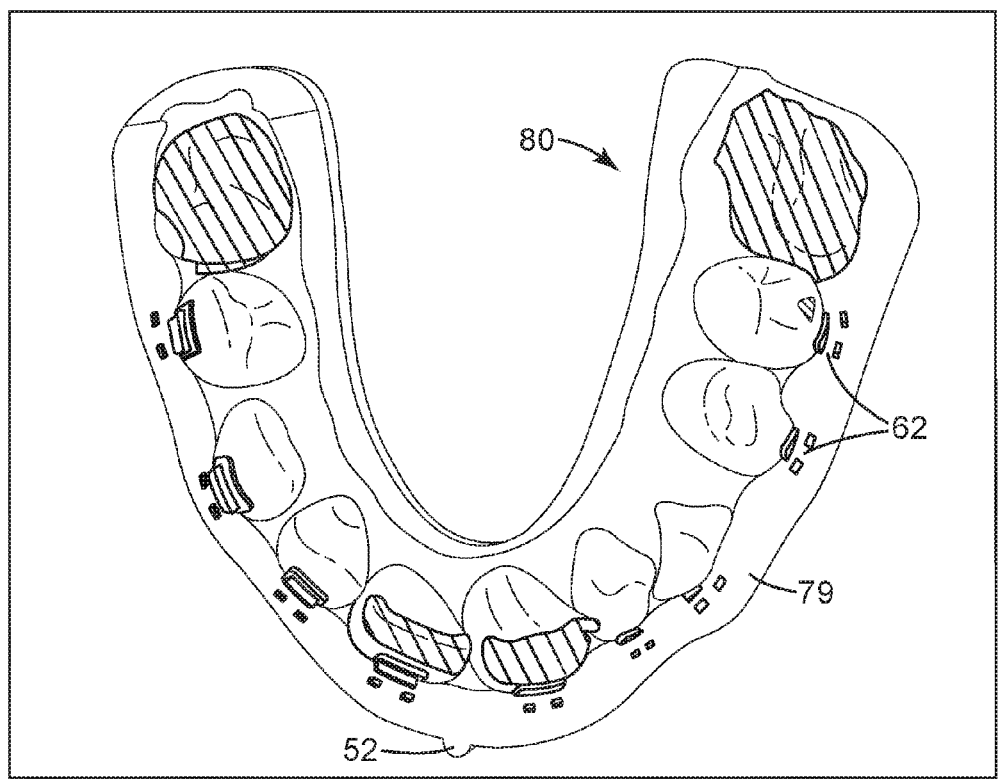
FIG. 11 is a gingival view of a virtual transfer tray formed by defining a cutting surface and virtually removing portions of the raw tray assembly of FIG. 10 located gingival to the cutting surface.

In block 114, a finished virtual transfer tray 80 is produced by trimming the tray assembly 70 to create a gingival edge 79 that intersects with one or more of the receptacles 62. This may be accomplished by defining a virtual cutting surface that intersects with one or more of the receptacles 62 and virtually removing a portion of the tray body 56 that is located in the gingival direction from the cutting surface. The virtual cutting surface, and the resulting gingival edge 79, generally extend in an occlusal plane, but rise and fall in correspondence with the occlusal-gingival position of each receptacle. FIG. 11 shows a gingival view of the transfer tray 80 after completion of the above cutting operation. As shown, the gingival edge 79 intersects each receptacle 62 in tray body 56.

Figure 11A:
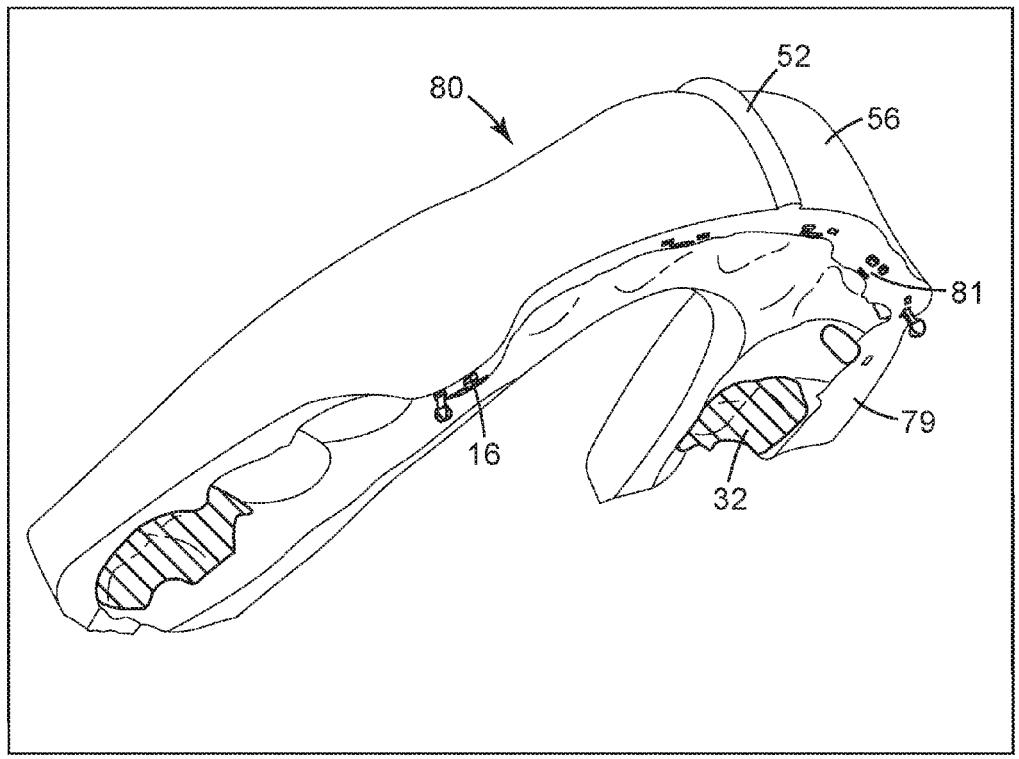
FIG. 11a is a lingual view of the tray in FIG. 11, with virtual appliances in place.

FIG. 11a shows a facial view of the transfer tray 80, with virtual appliances 16 in place. From this view, it is observed that transfer tray 80 has a configuration in which the gingival edge 79 generally rises and falls based on the occlusal-gingival positions of appliances 16 along the dental arch. In some embodiments, the gingival edge 79 generally rises and falls based on the occlusal-gingival positions of three or more appliances 16 along the dental arch. Optionally and as shown, each receptacle 62 has a configuration that extends across at least some of the facially-oriented surfaces of its respective appliance 16. When the tray 80 is virtually engaged to the model 10, the tray body 56 therefore extends across at least a portion of the model 10 and at least a portion of each receptacle 62 remote from the model 10.

This configuration of tray 80 provides numerous advantages that are realized in the resultant physical transfer tray. First, it helps minimize the distance traveled by the resultant physical transfer tray over the patient's teeth during tray engagement. Minimizing this travel distance, in turn, helps minimize the potential to smear, or otherwise interfere with, adhesives applied to the teeth during bonding. This situation may be encountered, for example, when using a two-component (or AB type) chemical cure adhesive where one adhesive component is applied to the appliance and the other component is applied to the tooth. By reducing the surface area of the tray 80 located in the gingival direction from the appliances 16, less adhesive smearing can potentially occur on the tooth side when sliding the resultant physical transfer tray onto the patient's teeth from the occlusal direction. It is generally desirable to reduce the degree of adhesive smearing, since smearing can deplete the amount of adhesive at the bonding site and thereby decrease bond reliability.

Second, trimming the tray 80 in the manner described above helps to minimize undue contact between the resultant physical transfer tray and the patient's gingiva. Contact between the physical transfer tray and gingiva is preferably avoided because it is unnecessary and introduces the risk of a mismatch between the gingival tissue and the tray, which can interfere with proper tray seating. Further, the gingiva is a potential source of moisture in the patient's oral cavity. If moisture is present on these surfaces, contact between the gingiva and the physical transfer tray can result in seepage of saliva into the bonding site, which can again result in decreased bond reliability.

It is noted that the above steps in blocks 102,104,106, 108,110,112,114 represent just one possible sequence of steps used to produce the finished virtual transfer tray. Further steps or substitutions of the above steps may be used to accomplish the same result. Moreover, the steps described need not be executed in the exact order shown above. For example, the step of deriving of the stop members 32 in block 104 may be performed either before or after the step of deriving the outer surface 50 in block 106 if so desired.

Figure 12:
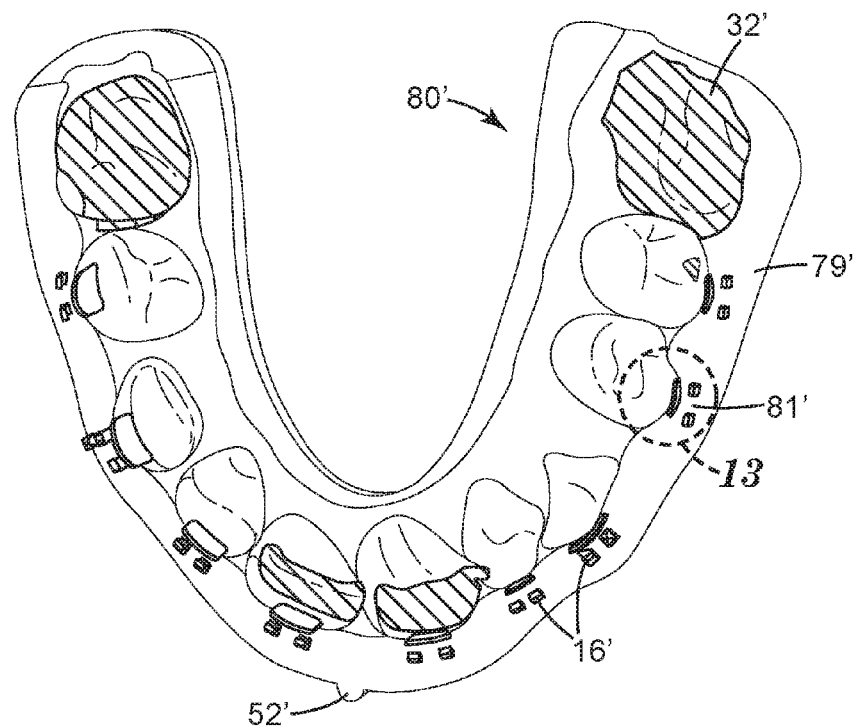
FIG. 12 is a gingival view of a physical transfer tray corresponding to the virtual transfer tray of FIGS. 11 and 11a, with physical appliances in place.

Block 116 and FIG. 12 show the fabrication of a physical transfer tray 80' from the virtual transfer tray 80 using rapid prototyping techniques. As used herein, "rapid prototyping" is a process that takes virtual designs from computer aided design (CAD) or other modeling software, transforms them into a series of thin, virtual, horizontal cross-sections and then re-constructs each cross-section in physical space, one after the next until the model is finished. For example, a rapid prototyping machine may read in data from a CAD drawing and lay down successive layers of liquid, powder, or sheet material, in order to build up the physical model. By automatically aligning and fusing together a series of cross-sections, the virtual model and physical model can correspond almost identically. Advantageously, the layer-by-layer aspect of rapid prototyping allows the creation of nearly any shape or geometric feature. As an added benefit, rapid prototyping also provides flexibility to fabricate articles that include two or more interpenetrating components with substantially different material properties.

Particular examples of "rapid prototyping" techniques include, but are not limited to, three-dimensional (3D) printing, selective area laser deposition or selective laser sintering (SLS), electrophoretic deposition, robocasting, fused deposition modeling (FMD), laminated object manufacturing (LOM), stereolithography (SLA) and photostereolithography. Issued U.S. Pat. Nos. 5,340,656, 5,490,882, 5,204,055, 5,518,680, 5,490,962, 5,387,380, 5,700,289, 5,518,680, and 4,672,032 describe examples of suitable rapid prototyping techniques. Particularly suitable rapid prototyping machines include the VIPER brand SLA system from 3D Systems (Rock Hill, S.C.) and EDEN brand 500V printer from Objet Geometries Ltd. (Rehovot, ISRAEL).

Once fabricated, the resulting physical transfer tray 80' is ready to be loaded with one or more appliances 16'. Each appliance 16' is manually or automatically placed into its respective receptacle 62' of the tray 80' to produce the assembly shown in FIGS. 12-14. If accurately fabricated, the tray 80' is an exact physical replica of the virtual tray 80. As shown, the tray 80' includes a physical stop member 32' (along with a physical flexible section 34'), physical tray body 56', and physical mid-line marker 52'. Preferably, the stop member 32' and the tray body 56' are composed of materials that facilitate the accurate and reproducible seating of the physical transfer tray 80' against the patient's teeth. When fully seated against the patient's dental structure, the stop member 32', along with the tray 80', assumes a unique position and orientation with respect to the dental structure. Such control is highly advantageous in precisely positioning physical appliances 16' in desired locations. As the tray 80' is urged in the gingival direction and seated against the patient's dental structure, the stop member 32' additionally provides a clear, tactile sensation that indicates the tray 80' has been fully seated due to the relatively hard nature of the stop member 32'.

As an added benefit, the stop member 32' can also be used to tailor the stiffness and resilience of the finished transfer tray 80'. Optionally and as shown in FIGS. 5 and 6, the cross-section of the flexible section 34' is rectangular in shape when considered in a plane perpendicular to its longitudinal axis, with an occlusal-gingival dimension greater than its lingual-facial dimension. The aspect ratio of the flexible section 34' is advantageous because it allows the tray 80' to be preferentially stiffened along particular directions. In this example, the stiffness of the transfer tray 80' along the longer cross-sectional dimension of the flexible section 34' (or occlusal-gingival directions) is significantly increased to minimize sagging of the tray 80' due to gravity when engaged to the teeth. On the other hand, stiffness is increased to a much lesser degree along the shorter cross-sectional dimension of the flexible section 34' (or lingual-facial directions), thereby facilitating transverse deflection of the tray. Easy deflection of the tray in the transverse directions provides the advantage of facilitating both engagement and disengagement of the transfer tray 80' in the mouth.

In some embodiments, the tray body 56' is formed from a first rapid prototyping material with a certain stiffness.

Stiffness, in turn, may be characterized using any number of methods, including Shore A hardness, Shore D hardness, tensile stress at 20 elongation, and tensile stress at 50 percent elongation. Preferably, the tray body 56' has a tensile stress at 20 percent elongation (according to ASTM D 412) that is in the range of about $0.4 \times 10^6$ to about $6.5 \times 10^6$ Pascal, more preferably in the range of about $0.8 \times 10^6$ to about $3.3 \times 10^6$ Pascal and most preferably in the range of about $1.1 \times 10^6$ to about $1.4 \times 10^6$ Pascal, and has a tensile stress at 50 percent elongation that is in the range of about $0.8 \times 10^6$ to about $12.5 \times 10^6$ Pascal, more preferably in the range of about $1.6 \times 10^6$ to about $6.2 \times 10^6$ Pascal and most preferably in the range of about $2.8 \times 10^6$ to about $3.4 \times 10^6$ Pascal. An example of a suitable material for the tray body 56' has a tensile stress at 20 percent elongation of about $1.3 \times 10^6$ Pascal and a tensile stress at 50 percent elongation of about $3.1 \times 10^6$ Pascal.

Optionally, the stop member 32' is formed from second rapid prototyping material with a stiffness greater than the certain stiffness of the tray body 56' material above. Preferably, the stop member 32' has a Shore A hardness that is greater than about 72, more preferably has a Shore A hardness that is greater than about 90, even more preferably has a Shore D hardness that is greater than about 60 and most preferably has a Shore D hardness that is greater than about 75. A suitable material for the stop member 32' may have, for example, a hardness of 72 Shore A hardness.

Optionally, the materials used to make the stop member 32' and tray body 56' transmit visible light to allow the appliances 16' to be seen when the tray 80' is engaged to a patient's teeth during bonding. Using materials that transmit light not only assists in determining the tray is fully seated, but also allows light curable adhesives (if used) to be cured by directing actinic radiation through the tray body 56'.

Figure 14:
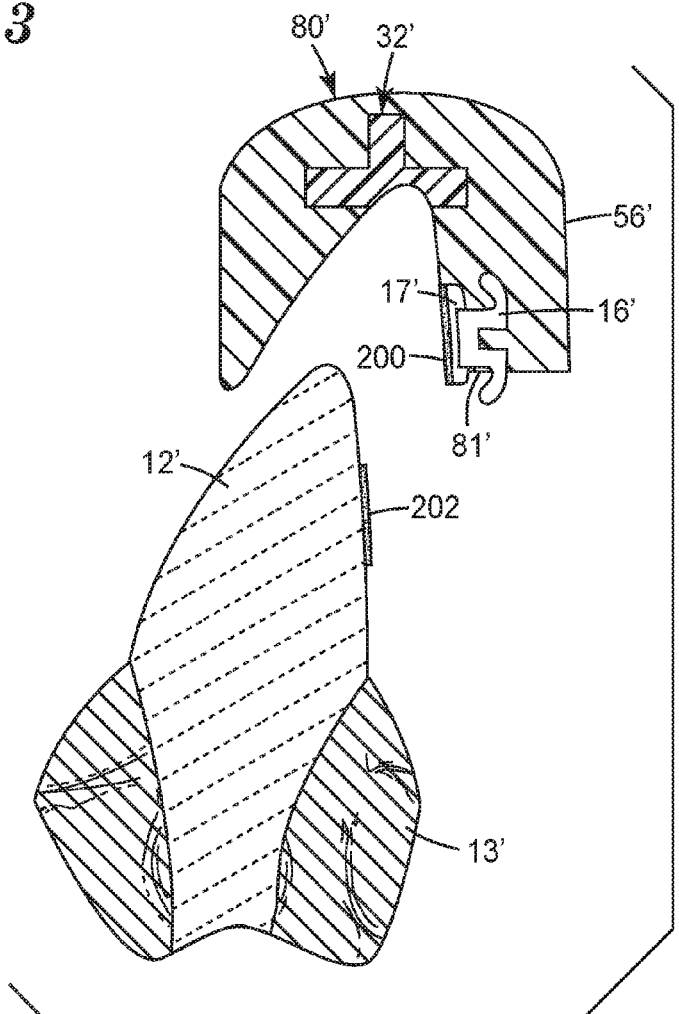
FIG. 14 is a side cross-sectional view of the tray illustrated in FIG. 13 after the tray has been detached from the dental arch model and trimmed, and further depicting the tray as it might appear immediately before placing the tray over the patient's dental structure.

FIG. 14 illustrates an exemplary use of the appliance-loaded transfer tray 80' in an indirect bonding procedure. For clarity, the steps described herein are directed to bonding a single appliance 16' to a respective tooth 12'. This method, however, may be easily extended to bond an entire set of appliances 16' to a plurality of teeth 12'. First, the patient's teeth 12' that are to receive the appliances 16' are isolated using cheek retractors, tongue guards, cotton rolls, dry angles and/or other articles as needed. The exemplary tooth 12' is then thoroughly dried using pressurized air from an air syringe. Etching solution (such as TRANSBOND XT brand etching gel from 3M Unitek Corporation) is then dabbed onto the tooth 12' in the general area that is to be covered by the appliance 16', taking care to prevent the etching solution from flowing into interproximal contacts or engaging the skin or surrounding gingiva 13'.

After the etching solution has remained on the selected tooth surfaces for a period of approximately 15-30 seconds, the solution is rinsed away from the tooth 12' with a stream of water for 15 seconds. The patient's teeth are then dried by the application of pressurized air from an air syringe (for example, for a time period of 30 seconds) and excess water is removed by suction. Care should also be undertaken to ensure that the saliva does not come into contact with the etched enamel surface. Cotton rolls or other absorbent devices are replaced as needed, again making sure that the saliva does not contact the etched enamel. Air from the air syringe may then be applied to the tooth 12' again to ensure that the tooth 12' is thoroughly dried. Optionally, the tooth 12' may be primed using, for example, TRANSBOND brand Moisture Insensitive Primer by 3M Unitek Corporation (Monrovia, Calif.).

Next, a bonding adhesive is applied to the bonding pad of the appliances 16' and/or the selected areas of the patient's tooth 12'. Optionally and as shown, the bonding adhesive is a two-component adhesive. The two-component adhesive may include, for example, a first component 200 such as SONDHI RAPID SET brand resin A and a second component 202 such as SONDHI RAPID SET brand resin B, both from 3M Unitek Corporation. The first component 200 is applied to the tooth-facing surface of the base 17' of the appliance 16' and the second component 202 is applied to the area of the patient's tooth 12' that is to receive the corresponding appliance 16'.

After the first component 200 has been applied to the bonding pad and the second component 202 has been applied to corresponding areas of the patient's tooth 12', the tray 80' is ready for seating. First, the tray 80' is oriented such that mid-line marker 52' is visually aligned with the shared boundary between the two central teeth 12' (patient's mid-line). Then the tray 80' is then urged in the gingival direction into mating engagement with the teeth 12'. Since the inner surfaces of the tray body 56' and the occlusal stop member 32' together match the shape of the underlying tooth 12', the appliance 16' is simultaneously seated onto the tooth 12' at the precise location corresponding to the previous position of the virtual appliance 16 on the virtual model 10.

When the tray 80' is constructed using the preferred materials mentioned above, it has been observed that the tray 80' "snaps" into place as the inner surfaces of the tray 80' engage the teeth 12' of the patient's dental arch. The tray 80' may be sufficiently stiff to press the appliances 16' against the tooth 12' as the adhesive cures without the application of external pressure. However, as an option, external pressure may be applied to the occlusal and facial surfaces of the tray 80' until such time as the bonding adhesive has sufficiently hardened. For example, finger pressure may be used to firmly press the appliances 16' against the facial surfaces of the patient's tooth 12'.

Other examples of suitable two-component chemical curing adhesives include UNITE brand adhesive and CONCISE brand adhesive, both from 3M Unitek Corporation. As an alternative, a resin-modified glass ionomer cement may be employed. As yet another option, a photocurable adhesive may be used, such as TRANSBOND XT brand adhesive or TRANSBOND LR brand adhesive, both from 3M Unitek Corporation. Other examples of suitable photocurable adhesive materials are described in U.S. Pat. No. 7,137,812 (Cleary et al.), U.S. Pat. No. 7,449,499 (Craig et al.) and U.S. Pat. No. 7,452,924 (Aasen et al.) as well as in pending U.S. Patent Publication No. 2005/0175966 (Falsafi et al.). The transfer tray 80' may also be packaged with appliances that are precoated with adhesive by the manufacturer, as described in U.S. Pat. No. 7,137,812 (Cleary et al.). An alternative method for applying primer to the patient's teeth 12' is described in U.S. Pat. No. 7,168,950 (Cinader, Jr., et al.) Once the bonding adhesive has hardened, the bonding tray 80' is carefully removed from the patient's dental arch.

In some embodiments, the receptacles 62' are open-ended in a generally gingival direction to facilitate occlusal detachment of the transfer tray 80' from the appliances 16'. By adopting a configuration where the receptacles are completely open-ended in the gingival direction, there is minimal interference between the tray body 56' and the appliances 16' when the tray is urged in the occlusal direction. In the embodiment shown in FIGS. 12-14, however, the virtual receptacles 62' are partially open-ended. Partially open-ended receptacles 16' allow gingival portions of the appliances 16' to protrude through the gingival edge 79' with the added advantage of firmly retaining the appliances 16' in the tray 80'. More particularly, tray body 56' includes a thin frangible web 81' that extends along the gingival edge 79' and is located in the gingival direction from the receptacles 62'. The frangible web 81' is sufficiently pliable to allow some degree of outward stretching in the gingival direction, thereby allowing appliances 16' to be loaded into the receptacles 62' from the lingual direction. Preferably, the frangible web 81' has both sufficient strength and sufficient rigidity to retain the appliances 16' in a precise position relative to the tray 80'.

Figure 13:
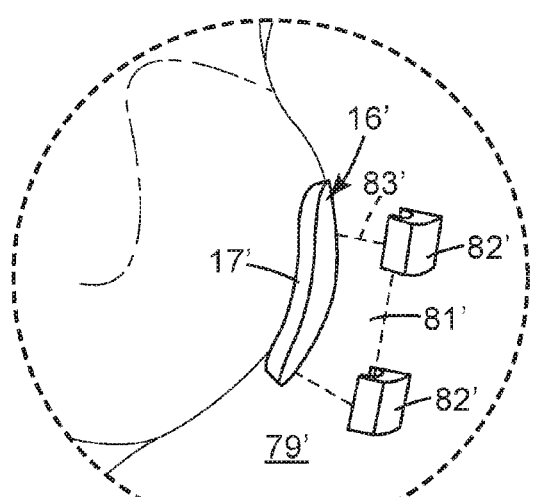
FIG. 13 is a close up view of a physical appliance placed in the physical transfer tray of FIG. 12, taken from the portion designated "13" in FIG. 12.

FIG. 13 shows an enlarged view of the frangible web 81' retaining an exemplary appliance 16' in transfer tray 80'. The appliance 16' includes two gingival tiewings 82' and a base 17' that partially protrude through the gingival edge 79' of the tray 80'. In this enlarged view, it can be seen that the frangible web 81' is formed by portions of the tray body 56' that extend between the protruding gingival tiewings 82' and base 17'. The web 81' optionally includes lines of weakness 83' that are indicated by dotted lines and extend between each tiewing 82' and the base 17' and between the two protruding tiewings 82'. The lines of weakness 83' indicate locations along which the web 81' is likely to fracture when the appliance 16' is urged towards the gingival direction with a sufficient amount of force. Optionally, the lines of weakness 83' may include notches, perforations, dimples, or combinations of these which act to concentrate stress along these areas and facilitate fracture of the web 81'.

Once the transfer tray 80' has been placed in a patient's mouth and appliances 16' bonded to the patient's dental structure, the tray 80' can be removed from the teeth 12' by urging the tray 80' in a generally occlusal direction and fracturing a portion of the tray 80' that extends across at least a portion of a gingival side of the receptacles 62'. Preferably, this fracture occurs along one or more lines of weakness 83' on the web 81'. Fracturing the web 81' furthermore facilitates the subsequent disengagement of the tray 80' from the now-bonded appliances 16' by sliding the tray 80' in a generally occlusal direction. It is noted that the lines of weakness 83' shown are exemplary and it is not necessary that the web 81' fractures along all of these lines. Preferably, the fractured portions of the web 81' still remain connected to the tray body 56' to prevent pieces of the tray 80' from falling into the oral cavity of the patient.

There are particular advantages to using receptacles 62' that are partially or fully open-ended along the gingival edge 79'. Partially or fully open-ended receptacles 62' allow for occlusal removal of the tray 80', which is not only convenient for the treating professional but also helps to avoid directing tensile forces (i.e., forces in the labial direction) to the adhesive during removal. This is advantageous since the tensile strength of orthodontic adhesives can be somewhat weak immediately after curing, and so tensile forces can cause appliances 16' to be accidentally debonded from the teeth 12'. The shear strength of orthodontic adhesives, by comparison, is comparably stronger. Occlusal removal of the tray 80' is also more comfortable for the patient, compared with the facial removal of conventional transfer trays.

Figure 15:
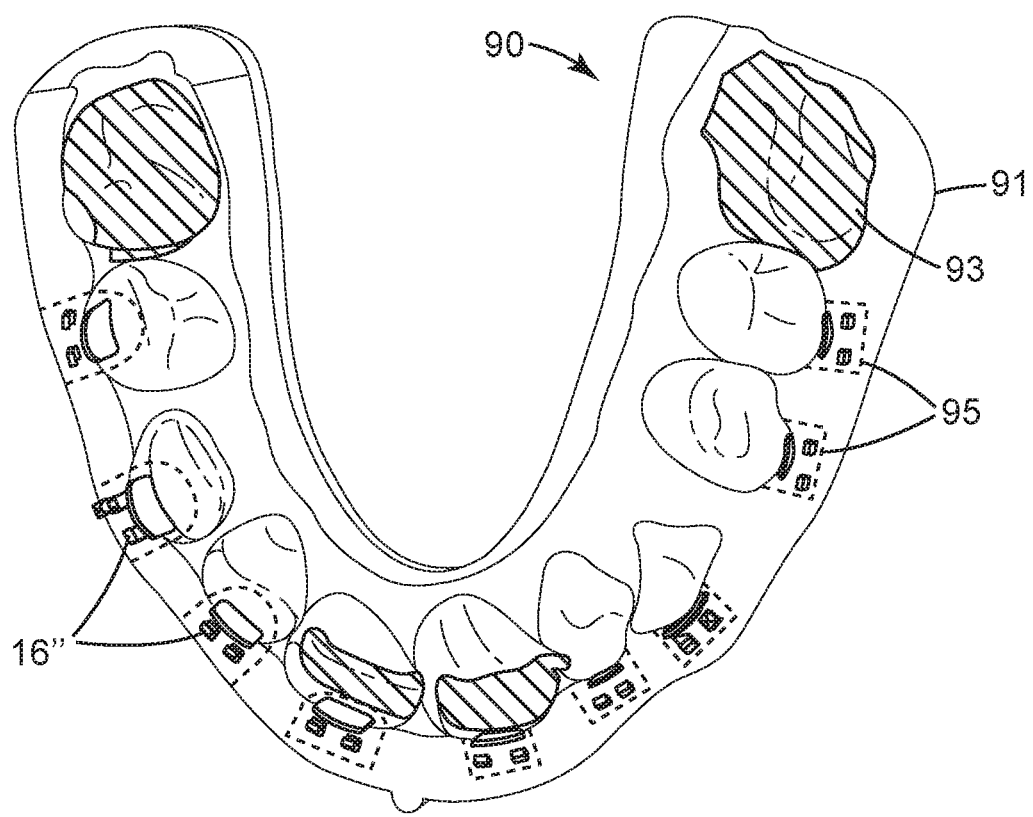
FIG. 15 is a gingival view of a physical transfer tray according to another embodiment of the invention.

FIG. 15 illustrates an alternative transfer tray embodiment. Transfer tray 90 includes a tray body 91 and stop member 93 that matches teeth 12 of the dental model 10. However, tray 90 further includes a third rapid prototyping material confined within regions 95 that surround each of a plurality of appliances 16". The third material in regions 95 has a stiffness that is less than the stiffness of either the stop member 32 or the tray body 56. Preferably, the material in regions 95 has a tensile stress at 20 percent elongation (according to ASTM D 412) that is in the range of about 31,000 to about 496,000 Pascal, more preferably in the range of about 62,000 to about 248,000 Pascal and most preferably in the range of about 112,000 to about 136,000 Pascal, and has a tensile stress at 50 percent elongation that is in the range of about 91,000 to about 1,460,000 Pascal, more preferably in the range of about 183,000 to about 730,000 Pascal and most preferably in the range of about 329,000 to about 402,000 Pascal. An example of a suitable material in regions 95 has a tensile stress at 20 percent elongation of about 124,000 Pascal and a tensile stress at 50 percent elongation of about 365,000 Pascal.

This configuration is advantageous because the softer material in regions 95 further facilitates detaching the physical appliances 94 from the transfer tray 90 after bonding. The flexibility of the material in the regions 95 also reduce the chances of inadvertently detaching the appliances 94 from the patient's teeth as transfer tray 90 is disengaged from the patient's dental structure after bonding. Methods for rendering and configuring the tray 90 in the virtual world, manufacturing the physical tray 90, and associated advantages, are similar to those already described for tray 80' and shall not be repeated here.

Finally, in the above detailed description, the trays 80',90 are presented for the bonding of labial appliances to the front side of teeth. While not explicitly shown, it is to be understood that the trays 80',90, and the methods of making them, can be easily adapted for the indirect bonding of lingual appliances.

EXAMPLE

An exemplary transfer tray was prepared using a scanned 3D virtual model of a patient as well as the 3D solid models of an upper 5×5 set of VICTORY SERIES brand orthodontic brackets (3M Unitek, Monrovia, Calif.) provided in STL format. A virtual model of the patient's arch was obtained using a digital scan of an orthodontic stone impression of a patient's upper dental arch. THREE-MATIC software (Materialise Group in Leuven, Belgium) was then used to construct a virtual model of the transfer tray. The 5×5 set of upper orthodontic brackets was virtually bonded to the model. A three-section integral stop member was derived to matingly engage the occlusal contours of the left first molar, right first molar and the left and right central teeth. A single guidance line was manually traced along the facial surfaces of the virtual brackets by an operator, and this guidance line was subsequently used to derive a smoothed outer surface that was offset by 3.5 millimeters in the labial direction from the model teeth and appliances. The virtual outer surface was filled using an extrusion process to form the tray body, and the tray precursor was formed by performing a Boolean subtraction between the model with appliances and the tray body. The integral stop member was then merged with the tray precursor, and a cutting surface used to define a gingival edge of the tray intersecting the bracket receptacles.

A physical transfer tray was then formed from the virtual transfer tray model using an EDEN 500V brand 3-Dimensional Printing System (Objet Geometries, Ltd., Rehovot, ISRAEL) A soft, pliable "Tango Plus" FULLCURE brand printing resin was used for the tray body, while a relatively hard "Fullcure 720" resin (also from Objet Geometries, Ltd.) was used for the occlusal stop member. After fabrication, the transfer tray was rinsed in water to dissolve the support material and then loaded with the physical orthodontic brackets. The finished transfer tray was observed to complementary engage over the stone replica model with no difficulties.

All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

The invention claimed is:

1. A transfer tray for use in bonding of a plurality of orthodontic appliances, each having a base for bonding to a tooth surface and a body extending outwardly from the base, the tray comprising:

a plurality of receptacles for the plurality of orthodontic appliances, each of the plurality of receptacles having a configuration matching a portion of the appliance body to releasably retain the appliance;

the plurality of orthodontic appliances releasably retained in the plurality of receptacles; and a tray body extending continuously across the plurality receptacles and having a gingival edge, wherein the gingival edge intersects each of the plurality of receptacles such that a first portion of each appliance body extends below the gingival edge and is not enclosed by any portion of the tray body for each appliance releasably retained in each receptacle, and wherein each receptacle and the tray body cooperate to cover all exterior surfaces of each appliance body opposite the base and located in an occlusal direction from the gingival edge each the appliance releasably retained in each receptacle, wherein positions of the receptacles in the tray body correspond with positions of teeth to receive the appliances retained in the receptacles.

2. The transfer tray of claim 1, wherein the tray body comprises rapid prototyping material.

3. The transfer tray of claim 1, wherein the tray body further includes an occlusal stop member and wherein the tray body has a first Shore hardness and the stop member has a second Shore hardness that is greater than the first Shore hardness.

4. The transfer tray of claim 1, wherein each receptacle is open-ended in a generally gingival direction to facilitate occlusal detachment of the transfer tray from the plurality of orthodontic appliances.

5. The transfer tray of claim 1, wherein the tray body further includes a frangible web that extends across at least a portion of the gingival side of each receptacle.

* * * * *

UNITED STATES PATENT AND TRADEMARK OFFICE
CERTIFICATE OF CORRECTION

| | | |
|---|---|---|
| PATENT NO. | : 10,492,889 B2 | Page 1 of 1 |
| APPLICATION NO. | : 15/261281 | |
| DATED | : December 3, 2019 | |
| INVENTOR(S) | : Kim et al. | |

It is certified that error appears in the above-identified patent and that said Letters Patent is hereby corrected as shown below:

In the Claims

Column 17
Line 25, in Claim 1, before "receptacles" insert -- of --.

Column 18
Line 7, in Claim 1, after "edge" insert -- for --.
Line 7, in Claim 1, before "appliance" delete "the".
Line 9, in Claim 1, after "wherein" insert -- prior to placement of the appliances on the teeth while the appliance are retained in the receptacles of the tray body, --.

Signed and Sealed this
Eighteenth Day of February, 2020

Andrei Iancu
*Director of the United States Patent and Trademark Office*